United States Patent [19]

Bird et al.

[11] Patent Number: 5,449,764
[45] Date of Patent: Sep. 12, 1995

[54] ISOLATED DNA DERIVED FROM PEACH WHICH CODES FOR AN ETHYLENE-FORMING ENZYME

[75] Inventors: Colin R. Bird, Bracknell, England; John A. Ray, Wooden Hill; Wolfgang W. Schuch, Heathlake Park, both of United Kingdom

[73] Assignee: Zeneca Limited, London, England

[21] Appl. No.: 78,176

[22] PCT Filed: Dec. 19, 1991

[86] PCT No.: PCT/GB91/02273

§ 371 Date: Aug. 10, 1993

§ 102(e) Date: Aug. 10, 1993

[87] PCT Pub. No.: WO92/11372

PCT Pub. Date: Jul. 9, 1992

[30] Foreign Application Priority Data

Dec. 20, 1990 [GB] United Kingdom ............... 9027616

[51] Int. Cl.⁶ .............. A01H 5/00; C12N 15/11; C12N 15/29; C12N 15/52
[52] U.S. Cl. .................. 536/23.2; 536/23.6; 536/25.3; 536/24.5; 435/172.1; 435/172.3; 800/200; 800/205; 800/DIG. 65
[58] Field of Search .............. 800/200, 205, 250, 255, 800/DIG. 65; Plt. 42.1; 435/172.1, 172.3, 240.4; 935/56, 35; 536/23.2, 23.6, 25.3, 24.5

[56] References Cited

U.S. PATENT DOCUMENTS

P.P. 6,409  11/1988  Zaiger et al. .............. Plt./42.1

OTHER PUBLICATIONS

Potrykus, 1991, Annu. Rev. Plant Physiol. Plant & Mol. Biol. 1991, 42:205–225.
Von der Krol et al. 1988, Nature, 333:865–869.
Holdsworth et al. 1987a Nucleic Acids Research, 15(2):731–739.
Holdsworth et al. 1987b, Nucleic Acids Research 15(24):10600.
Holdsworth et al. 1988, Plant Molecular Biology, 11:81–88.
Hamilton et al. 1990, Nature, 346:284–287.
Callahan et al. 1990a, Journal of Cellular Biochemistry Suppl. 14E:346 Abstract #R505.
Callahan et al. 1990b, Hortscience 25(9):130–131 Abstract #478.
Morgens et al. 1990, In Current Topics in Plant Physiology vol. 5 Flores et al., eds. pp. 319–320.
Giovannori et al. 1989, The Plant Cell 1:53–63.

*Primary Examiner*—David T. Fox
*Assistant Examiner*—Erich E. Veitenheimer
*Attorney, Agent, or Firm*—Cushman Darby & Cushman

[57] ABSTRACT

DNA clones, e.g. P13-B, comprising at least part of a gene derived from peach that encodes ethylene-forming enzyme. Such clones may comprise DNA constructs including plant promoters capable of expressing RNA in plant cells. Such constructs may be used to inhibit production of ethylene-forming enzyme in transformed plants, and thereby to produce slower-ripening fruit, particularly peaches. The clones may be obtained by PCR using specific oligo-nucleotide primers.

2 Claims, 3 Drawing Sheets

FIG.1

SEQ ID NO: 1
SEQUENCE TYPE: Nucleotide
SEQUENCE LENGTH: 580 base pairs

STRANDEDNESS: single
TOPOLOGY: linear
MOLECULE TYPE: DNA

ORIGINAL SOURCE ORGANISM: Peach fruit
IMMEDIATE EXPERIMENTAL SOURCE: Polymerase chain reaction of genomic DNA FEATURES:
from 1 to 23 bp    PCR primer
from 1 to 27 bp    exon
from 28 to 188 bp  intron
from 189 to 580 bp exon
from 559 to 580 bp PCR primer PROPERTIES: P13-B : Fragment of peach genomic DNA with homology to tomato pTOM13

```
GCATGTGAGA ATTGGGGGTT TTTGAGGTAA ACCAACCTTT AGCTGCTTTG AGATATTTTT   60
ATTTCTTTTA AAGCTTTGAT GAGAAGTCAG CCAGTTAATT ACAAATGATG TTTTTTTCTT  120
TCTATATCAC GATCATCTGT GTTTCTAATA ATAACTCTTT TTTTAAATGT ACGAATTAAT  180
TAATGAAGTT GGTGAACCAT GGGATATCTC ATGAGCTGAT GGATACTGTG GAGAAGCTGA  240
CAAAGGAGCA CTACAAAAAG TGCATGGAGC AAGGTTTAA GGAAATGGTC GCAAGCAAAG   300
GCCTTGAAGC TGTCCAGTCT GAAATCCATG ACTTGGACTG GGAAAGCACC TTCTTCTTGC  360
GCCACCTTCC TGTCTCTAAC ATATCCCAAA TCCCTGACCT TGATGAAGAT TACAGGAAGG  420
TCATGAAAGA ATTTGCACTG GAATTAGAGA AACTAGCTGA GCAACTTCTG GACTTGCTGT  480
GTGAGAATCT TGGGTTGGAG AAGGGTTCTA TGAAGAAGGC TTTCTATGGA TCAAAGGGAC  540
CAAACTTCGG GACAAAGGTC AGCAACTACC CCCCATGCCC                       580
```

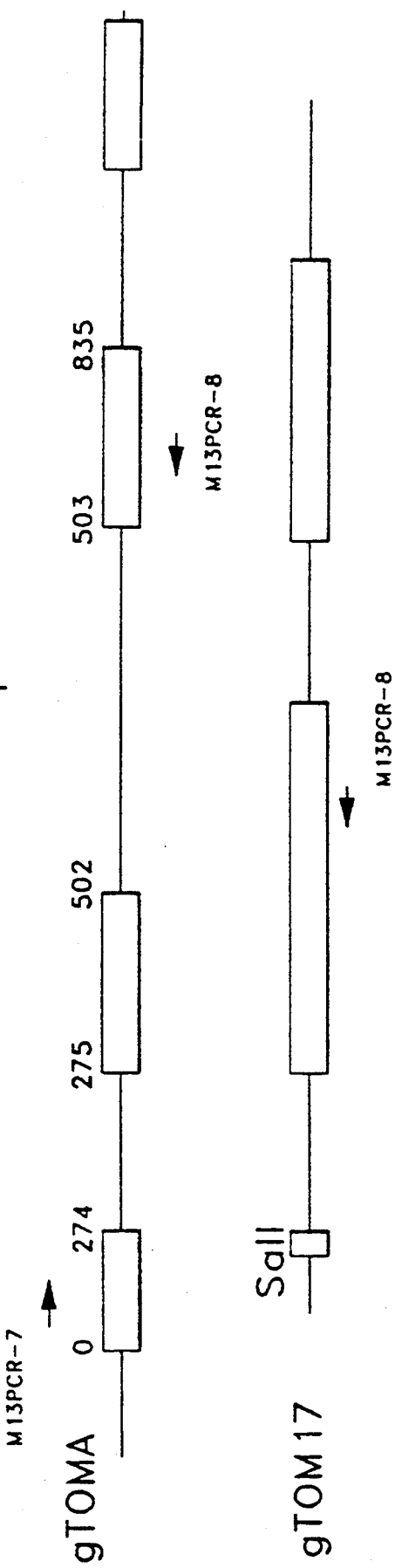
FIG. 2 ISOLATION OF MELON pTOM13 — OLIGO DESIGN

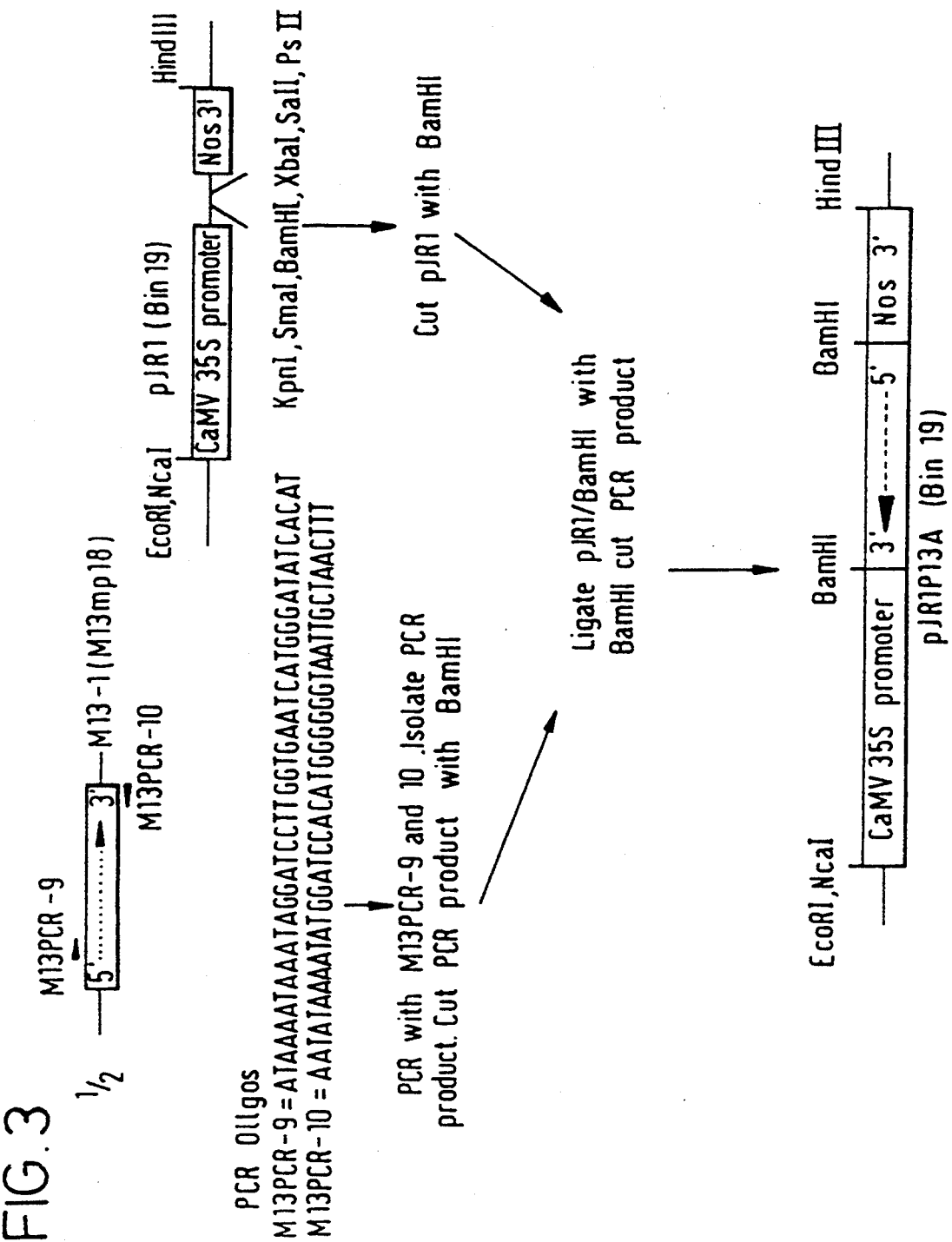

ISOLATED DNA DERIVED FROM PEACH WHICH CODES FOR AN ETHYLENE-FORMING ENZYME

BACKGROUND OF THE INVENTION

This application relates to novel DNA constructs, plant cells containing the constructs and plants derived therefrom. In particular it involves the use of antisense or sense RNA technology to control gene expression in plants.

SUMMARY OF THE INVENTION

Many physiological and developmental processes are controlled by ethylene in higher plants, including peach (*Prunus persica*). These processes include fruit ripening where ethylene may be involved in both the initiation and rate of continuation of many of the changes involved in fruit ripening. However the exact role of ethylene has hitherto not been fully understood. We have now isolated novel DNA involved in the generation of ethylene in peaches. In this invention, we provide such novel DNA, and methods of using it. One such use is a method for controlling the rate of production of ethylene in ripening peaches. In this way the rate of many of the ethylene-related changes associated with fruit ripening on a plant can be modified according to the characteristics that are required.

DESCRIPTION OF THE PREFERRED EMBODIMENTS

As is well known, a cell manufactures protein by transcribing the DNA of the gene for that protein to produce messenger RNA (mRNA), which is then processed (eg by the removal of introns) and finally translated by ribosomes into protein. This process may be inhibited by the presence in the cell of "antisense RNA". By this term is meant an RNA sequence which is complementary to a sequence of bases in the mRNA in question: complementary in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or degrade the mRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes has been described, in for example European Patent publication no 271988 to ICI (corresponding to U.S. Ser. No. 119614). Reduction of gene expression has led to a change in the phenotype of the plant: either at the level of gross visible phenotypic difference e.g. lack of anthocyanin production in flower petals of petunia leading to colourless instead of coloured petals (van der Krol et al, Nature, 333, 866–869, 1988); or at a more subtle biochemical level e.g. change in the amount of polygalacturonase and reduction in depolymerisation of pectins during tomato fruit ripening (Smith et al, Nature, 334, 724–726, 1988; Smith et al., Plant Molecular Biology, 13, 303–311, 1990) Thus antisense RNA has been proven to be useful in achieving downregulation of gene expression in plants.

The present invention relates to clones of a gene which expresses ethylene-forming enzyme (EFE). EFE is involved in ethylene production, and hence in the ripening of peaches (Tonutte et al., J. Am. Soc. Hort. Sci., 116, p274, 1991). Fragments of this gone have been cloned and characterised. We postulate that they will be of use in modifying the ripening characteristics of peaches. The gene in question is partially encoded in the-clone P13-B, which has homology (83% encoded amino acid homology) with the clone pTOM13 from tomato disclosed by Holdsworth et al (Nucleic Acids Research 15, 731, 1987). It has been shown that the gene encoded by pTOM13 is involved in ethylene synthesis in tomatoes (Hamilton et al, Nature, 346, pp284, 1990), and its translation product is now believed to be ethylene-forming enzyme (Hamilton et al., Proc. Nat. Acad>, Sci. USA, 88, p 7434, 1991).

According to the present invention we provide a DNA clone including at least part of a gene derived from peach that encodes ethylene-forming enzyme. One example of such a clone is clone P13-B. We further provide such DNA clones including DNA constructs comprising a DNA sequence homologous to to some or all of a gene derived from peach that encodes ethylene-forming enzyme, preceded by a transcriptional initiation region operative in plants, so that the construct can generate RNA in plant cells.

In a further aspect, the invention provides such DNA clones including DNA constructs, in which the homologous gene sequence is inverted with respect to the transcriptional initiation sequence so that the construct can generate in plant cells RNA antisense to mRNA for ethylene-forming enzyme. The invention also includes plant cells transformed with constructs derived from such clones; plants derived therefrom showing modified ripening characteristics; and fruit and seeds of such plants.

The clones of the invention may be used to transform plants to regulate the production of enzymes encoded by genes homologous to P13-B. Depending on the nature of the construct, the production of the enzymes may be increased, or reduced, either throughout or at particular stages in the life of the plant. Generally, as would be expected, production of the enzyme is enhanced only by constructs which express RNA homologous to the substantially complete endogenous P13-B mRNA. Constructs containing an incomplete DNA sequence substantially shorter than that corresponding to the complete gene generally inhibit the expression of the gene and production of the enzymes, whether they are arranged to express sense or antisense RNA.

The present invention can be applied to a variety of plants, and in particular to peaches. In this way, plants can be generated which have modified expression levels of genes with homology to P13-B and which have modified levels of ethylene production during ripening. In this way, the time of initiation and the rate of many of the ripening processes can be controlled, so as to give improved fruit quality.

Retardation of the rate of ripening will reduce the rate of deterioration of peach fruit after harvest. As a result of this fruit may be harvested when they have reached partial or full ripeness and still have the robustness to withstand handling and transport to reach the consumer in good condition. In this way high quality ripe fruit can be made available to the consumer with reduced requirement for post-harvest treatment. High quality fruit will have improved flavour and texture.

In addition high quality fruit can be produced consistently over a wide harvest period. Such fruit can be held in store for long periods and ripened to optimal quality by the supply of exogenous ethylene.

Antisense clones according to the invention preferably comprise a base sequence at least 10 bases in length for transcription into antisense RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

The preferred DNA for use in the present invention is DNA derived from the clone P13-B. The required antisense DNA can be obtained in several ways: by cutting with restriction enzymes an appropriate sequence of such DNA; by synthesising a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences. If it is desired to produce antisense DNA, the cloning being carried out that the cut DNA sequence is inverted with respect to its orientation in the strand from which it was cut.

In new vectors expressing antisense RNA, the strand that was formerly the template strand becomes the coding strand, and vice versa. The new vector will thus encode RNA in a base sequence which is complementary to the sequence of P13-B mRNA. Thus the two RNA strands are complementary not only in their base sequence but also in their orientations (5' to 3').

As source of the DNA base sequence for transcription, it is convenient to use clones such as P13-B. The base sequence of P13-B is set out in FIG. 1. This clone has homology to the tomato cDNA clone pTOM13 (Holdsworth et al, cited above) which encodes tomato ethylene-forming enzyme (Hamilton et al, Proc. Natl. Sci. Acad. USA, cited above). Tomato plants expressing antisense RNA to pTOM13 have reduced rates of ethylene synthesis in ripenlug fruit and wounded leaves.

P13-B has been deposited on 4 Oct. 1990 with the National Collections of Industrial and Marine Bacteria, 23 St Machat Drive, Aberdeen, Scotland, under Accession No. NCIB 40323.

Clones similar to P13-B may be obtained by using suitable oligonucleotide primers in a polymerase chain reaction (PCR) with peach genomic DNA. Suitable oligonucleotide primers may be designed according to methods similar to those described in Example 1. Such oligonucleotide primers can be used in PCR reactions with genomic DNA from other species or varieties as required. DNA fragments synthesised in these reactions may be either cloned into suitable vectors for further characterisation or cloned directly into vectors for expression in plants. Such fragments of genomic DNA may contain introns such as those found in P13-B. The introns are not transcribed into mRNA (or, if so transcribed, are subsequently cut out). When using such a gene as the source of the base sequence for transcription it is possible to use either intron or exon regions.

Alternatively, cDNA clones homologous to P13-B may be obtained from the mRNA of ripening peaches by well-known methods (kits for the purpose are available from various manufacturer, e.g., Amersham). In this ray may be obtained sequences coding for the whole, or substantially the whole, of the mRNA produced by P13-B. Suitable lengths of the cDNA so obtained may be cut out for use by means of restriction enzymes. cDNA clones may differ from the fragments of genomic DNA that are obtained by polymerase chain reaction in that any introns present in the genomic fragment will not be present in the cDNA. A further way of obtaining a suitable DNA base sequence for transcription is to synthesise it ab initio from the appropriate bases, for example using FIG. 1 as a guide.

Recombinant DNA and vectors according to the present invention may be made as follows. A suitable vector containing the desired base sequence for transcription (for example P13-B) is treated with restriction enzymes to cut the sequence out. The DNA strand so obtained is cloned (if desired, in reverse orientation) into a second vector containing the desired promoter sequence (for example cauliflower mosaic virus 35S RNA promoter or a peach fruit-ripening-specific promoter) and the desired terminator sequence (for example the 3' of the *Agrobacterium tumefaciens* nopaline synthase gene, the nos 3' end).

According to the invention we propose to use both constitutive promoters (such as cauliflower mosaic virus 35S RNA) and inducible or developmentally regulated promoters (such as the ripe-fruit-specific promoters) as circumstances require. Use of a constitutive promoter will tend to affect functions in all parts of the plant: while by using a tissue specific promoter, functions may be controlled more selectively. Use of such a promoter has the advantage that the production of antisense RNA is under the control of a ripening-specific promoter. Thus the antisense RNA is only produced in the organ in which its action is required.

Vectors according to the invention may be used to transform plants as desired, to make plants according to the invention. Dicotyledonous plants, such as peaches, may be transformed by Agrobacterium Ti plasmid technology, for example as described by Bevan (1984) Nucleic Acid Research, 12, 8711–8721. Other known transformation methods, such as particle gun technology, may be used where convenient. Such regenerated transformed plants may be reproduced sexually, or by cell or tissue culture.

The degree of production of antisense RNA in the plant cells can be controlled by selection of plants having a desired level of reduced ethylene synthesis. This can be achieved by suitable choice of promoter sequences, or by selecting the number of copies, or the site of integration, of the DNA sequences according to the invention that are introduced into the plant genome. In this way it may be possible to modify ripening or senescence to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants.

Our invention further comprises a process of isolating DNA of interest from a plant, which comprises preparing a plant DNA library, probing the cloned library with a probe comprising DNA from a clone according to the invention and recovering DNA that binds to the probe.

As well as their use in transforming plants, the clones and oligonucleotide primers disclosed herein may be used for other purposes. In particular, they may be used to identify other regions of plant DNA of interest, particularly from peaches or other Prunus species. Thus our invention includes processes for isolation and identification of DNA of interest from a plant. These processes use the clones as hybridisation probes to identify related sequences in libraries of cloned plant genomic DNA, e.g. cDNA. In addition, the oligonucleotide primers may be used in polymerase chain reactions to amplify related sequences. In this way may be recovered, from peach DNA for example, a number of other genes showing homology with P13-B. These may be partial or full length genomic or cDNA sequences encoding isozymes of peach ethylene-forming enzyme or other related oxidases. They may also include other gene elements, for example inducible promoters. It is very possible that the ethylene-forming enzyme produced in response to plant wounding is from a gene different from that which produces ethylene during fruit ripening: the clones of our invention may be used to isolate various members (isozymes) of the EFE gene family. In this way, the various physiological processes involving ethylene may be controlled by the methods described in this invention.

BRIEF DESCRIPTION OF THE DRAWINGS

The invention will now be described further with reference to the accompanying drawings, in which:

FIG. 1 shows the nucleotide sequence of P13-B (SEQ ID NO:1);

FIG. 2 is a diagram showing the design of oligonucleotide primers for PCR reactions to amplify fragments of pTOM13 -related genes from peach (OLIGO/M13PCR-7 is SEQ ID NO:2; OLIGO/M13PCR-8 is SEQ ID NO:3; pTOM13/M13PCR-7 is SEQ ID NO:6; gTOMA/M13PCR-7 is SEQ ID NO:7; pE8/M13PCR-7 is SEQ ID NO:8; pTOM13/M13PCR-8 is SEQ ID NO:9; gTOMA/M13PCR-8 is SEQ ID NO:10; and, pE8/M13PCR-8 is SEQ ID NO:11);

FIG. 3 is a diagram showing the construction of the clone pjR1P13A (M13PCR-9 is SEQ ID NO:4; and M13PCR-10 is SEQ ID NO:5).

EXAMPLE 1

Design of Oligonucleotides

Tomatoes contain at least three genes related to pTOM13 (GTOM17, GTOMA and GTOMB—see Holdsworth et al., Plant Mol. Biol., 11, pp 81–88, 1988). A further tomato ripening related gene sequence, E8, has been shown to have limited homology with pTOM13 (Deikman J. & Fischer R. L. EMBO J 7: 3315–3320 (1988)). Two oligonucleotide primers (M13PCR7 and M13PCR8) were designed (FIG. 2), based on regions of homology between pTOM13, GTOMA and E8 (see Holdsworth et al., Nucleic Acids Research, 15, p 10600, 1987), that could be used to amplify specific regions of the genes in polymerase chain reactions. These oligonucleotide primers can be used for amplification of related genes from other plant species.

EXAMPLE 2

Polymerase Chain Reactions with Peach Genomic DNA

Genomic DNA was prepared from a single peach fruit obtained from a local market by the method of Raeder and Broda (Lett Appl Microbiol 1, 17–20, 1985). Approximately 1ug genomic DNA was used in a PCR with oligonucleotides M13PCR7 and M13PCR8 (1 μg each). The temperature of the annealing step used in the reaction was 45° C. for 0.2 minutes. The resulting PCR products were made blunt ended using T4 DNA polymerase and cloned into M13 mp18 cut with SmaI. Plaque lifts were made onto 'Hybond' N(Amersham) nylon membranes. The filters were probed with 32P labelled pTOH13 at 42° C. and washed in 2×SSC, 0.1% SDS, at 42° C. Plaques which hybridised to pTOM13 were picked and DNA sequencing templates were prepared. The sequence obtained from five clones P13-B,C,D,E and F showed homology to the published sequence of pTOM13.

EXAMPLE 3

Construction of pJR1P13A

Oligonucleotides were designed to amplify, by PCR, an 389 bp fragment from P13-B (see Example 3) which contained all of the second exon and introduced BamHI sites at both ends of the PCR product. The oligonucleotides are used in a PCR with single stranded DNA from clone P13-B. The resulting PCR product is isolated from agerose cut with BamHI and ligated with pJR1 cut with BamHI. Colony lifts are made onto 'Hybond' N membranes and the filters probed with $^{32}$P-labelled pTOM13 at 42° C. After washing with 2×SSC, 0.1% SDS at 42° C., hybridising colonies are picked lysed and the orientation of the peach fragment in each clone is determined by PCR with oligo M13PCR10 and NOS. A clone containing the peach fragment in the antisense orientation is designated pJRP13A.

EXAMPLE 4

Generation of Transformed Plants

Vectors are transferred to *Agrobacterium tumefaciens* LBA4404 (a micro-organism widely available to plant biotechnologists) and are used To transform tomato and peach plants. Transformation of peach (Hammerschlag FA et al (1989) J Am Soc Hort Sci, 114, 508: see also Fong G and Grumet R, 1989, Plant Cell Reports 9, pp 160–164) tissue follows adaptations of protocols devised for other dicotyledonous plants. Transformed plants are identified by their ability to grow on media containing the antibiotic kanamycin. Plants are regenerated and grown to maturity. Ripening fruit are analysed for modifications to their ripening characteristics.

We claim:

1. An isolated DNA clone comprising a gene derived from peach that encodes ethylene-forming enzyme, said gene having the sequence found in clone P13-B (SEQ ID NO:1) in which said gene sequence is preceded by a transcriptional initiation sequence operative in plants, so that the clone can generate RNA in plant cells.

2. A DNA clone as claimed in claim 1 in which the gene sequence is inverted with respect to the transcriptional initiation sequence so that the clone can generate in plant cells RNA antisense to mRNA for ethylene-forming enzyme.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 580 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GCATGTGAGA  ATTGGGGGTT  TTTGAGGTAA  ACCAACCTTT  AGCTGCTTTG  AGATATTTTT    60
ATTTCTTTTA  AAGCTTTGAT  GAGAAGTCAG  CCAGTTAATT  ACAAATGATG  TTTTTTTCTT   120
TCTATATCAC  GATCATCTGT  GTTTCTAATA  ATAACTCTTT  TTTTAAATGT  ACGAATTAAT   180
TAATGAAGTT  GGTGAACCAT  GGGATATCTC  ATGAGCTGAT  GGATACTGTG  GAGAAGCTGA   240
CAAAGGAGCA  CTACAAAAAG  TGCATGGAGC  AAAGGTTTAA  GGAAATGGTC  GCAAGCAAAG   300
GCCTTGAAGC  TGTCCAGTCT  GAAATCCATG  ACTTGGACTG  GAAAGCACC   TTCTTCTTGC   360
GCCACCTTCC  TGTCTCTAAC  ATATCCCAAA  TCCCTGACCT  TGATGAAGAT  TACAGGAAGG   420
TCATGAAAGA  ATTTGCACTG  GAATTAGAGA  AACTAGCTGA  GCAACTTCTG  GACTTGCTGT   480
GTGAGAATCT  TGGGTTGGAG  AAGGGTTCTA  TGAAGAAGGC  TTTCTATGGA  TCAAAGGGAC   540
CAAACTTCGG  GACAAAGGTC  AGCAACTACC  CCCCATGCCC                           580
```

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
GATGCATGTG  AGAATTGGGG  NTTYTT                                            26
```

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
AAATCTGGTT  TAGGRCATGG  NGGRTA                                            26
```

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
ATAAAATAAA  TAGGATCCTT  GGTGAATCAT  GGGATATCAC  AT                        42
```

( 2 ) INFORMATION FOR SEQ ID NO:5:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

AATATAAAAT ATGGATCCAC ATGGGGGGTA ATTGCTAACT TT    42

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Asp Ala Cys Glu Asn Trp Gly Phe Phe
1                5

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Asp Ala Cys Glu Asn Trp Gly Phe Phe
1                5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Asp Ala Ser Glu Lys Trp Gly Phe Phe
1                5

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Tyr Pro Pro Cys Pro Lys Pro Asp Leu
1                5

( 2 ) INFORMATION FOR SEQ ID NO:10:

( i ) SEQUENCE CHARACTERISTICS:
        ( A ) LENGTH: 9 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

Tyr Pro Pro Cys Pro Lys Pro Asp Leu
1               5

(2) INFORMATION FOR SEQ ID NO:11:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

Tyr Pro Pro Cys Pro Gln Pro Glu Leu
1               5